US007855049B2

(12) United States Patent
Berggren et al.

(10) Patent No.: US 7,855,049 B2

(45) Date of Patent: Dec. 21, 2010

(54) INOSITOL PYROPHOSPHATES DETERMINE EXOCYTOTIC CAPACITY

(75) Inventors: Per-Olof Berggren, Solna (SE); Christopher Barker, Stockholm (SE)

(73) Assignee: BioCrine AB, Stockholm (SE)

(*) Notice: Subject to any disclaimer, the term of this patent is extended or adjusted under 35 U.S.C. 154(b) by 29 days.

(21) Appl. No.: 12/199,388

(22) Filed: Aug. 27, 2008

(65) Prior Publication Data

US 2009/0074743 A1 Mar. 19, 2009

Related U.S. Application Data

(60) Provisional application No. 60/969,443, filed on Aug. 31, 2007.

(51) Int. Cl.
*C12N 5/00* (2006.01)
*C12N 5/02* (2006.01)

(52) U.S. Cl. ........................... 435/4; 435/325; 435/375

(58) Field of Classification Search ..................... 435/4
See application file for complete search history.

(56) References Cited

U.S. PATENT DOCUMENTS 5,580,859 A 12/1996 Felgner et al.
5,589,466 A 12/1996 Felgner et al.
5,593,972 A 1/1997 Weiner et al.

FOREIGN PATENT DOCUMENTS

WO WO 90/11092 10/1990
WO WO 03/066087 8/2003
WO WO 2004/006838 1/2004

OTHER PUBLICATIONS

Zambre et al. (1999), "Inhibition of human pancreatic islet insulin release by receptor-selective somatostatin analogs directed to somatostatin receptor subtype 5." Biochem. Pharmacol. 57: 1159-1164.

Zhang et al. (1996), "Gene therapy with an adeno-associated virus carrying an interferon gene results in tumor growth suppression and regression." Cancer Gene Therapy 3: 31-38.

Barker et al. (2002), "Phosphorylated inositol compounds in beta -cell stimulus-response coupling." Am. J. Physiol. Endocrinol. Metab. 283: E1113-22.

Barker et al. (2004), "Complex changes in cellular inositol phosphate complement accompany transit through the cell cycle." Biochem. J. 380: 465-73.

Belldegrun et al. (1993), "Human renal carcinoma line transfected with interleukin-2 and/or interferon alpha gene (s): implications for live cancer vaccines." J. Natl. Cancer Inst. 85: 207-16.

Bennett et al. (2006), "Inositol pyrophosphates: metabolism and signaling." Cell Mol. Life Sci. 63: 552-64.

Berridge (1995), "Inositol trisphosphate and calcium signaling." Ann. N. Y. Acad. Sci. 766: 31-43.

Cejvan et al. (2003), "Intra-islet somatostatin regulates glucagon release via type 2 somatostatin receptors in rats." Diabetes 52: 1176-1181.

Efanov et al. (1997), "Inositol hexakisphosphate stimulates non-Ca2+-mediated and primes Ca2+-mediated exocytosis of insulin by activation of protein kinase C." Proc. Natl. Acad. Sci. USA 94: 4435-9.

Fagan et al. (1998), "Insulin secretion is inhibited by subtype five somatostatin receptor in the mouse." Surgery 124:254-8.

Fawell et al. (1994), "Tat-mediated delivery of heterologous proteins into cells." Proc. Natl. Acad. Sci. USA 91(2): 664-8.

Ferrantini et al. (1993), "Alpha 1-interferon gene transfer into metastatic Friend leukemia cells abrogated tumorigenicity in immunocompetent mice: antitumor therapy by means of interferon-producing cells." Cancer Research 53: 1107-1112.

Ferrantini et al. (1994), "IFN-alpha 1 gene expression into a metastatic murine adenocarcinoma (TS/A) results in CD8+ T cell-mediated tumor rejection and development of antitumor immunity. Comparative studies with IFN-gamma-producing TS/A cells." J. Immunology 153: 4604-4615.

Frankel et al. (1988), "Cellular uptake of the tat protein from human immunodeficiency virus." Cell 55(6): 1189-93.

Gillis et al. (1996), "Protein kinase C enhances exocytosis from chromaffin cells by increasing the size of the readily releasable pool of secretory granules." Neuron 16: 1209-20.

Green et al. (1988), "Autonomous functional domains of chemically synthesized human immunodeficiency virus tat trans-activator protein." Cell 55(6): 1179-88.

Ho et al. (2001), "Synthetic protein transduction domains: enhanced transduction potential in vitro and in vivo." Cancer Res. 61(2): 474-7.

Høy et al. (2002), "Inositol hexakisphosphate promotes dynamin I-mediated endocytosis." Proc. Natl. Acad. Sci. USA 99: 6773-7.

Høy et al. (2003), "Involvement of protein kinase C-epsilon in inositol hexakisphosphate-induced exocytosis in mouse pancreatic beta-cells." J. Biol. Chem. 278: 35168-71.

Illies et al. (2007), "Requirement of inositol pyrophosphates for full exocytotic capacity in pancreatic beta cells." Science 318(5854): 1299-302.

International Search Report for WO 09/027107, mailed on Dec. 29, 2008.

Irvine et al. (2001), "Back in the water: the return of the inositol phosphates." Nat. Rev. Mol. Cell Biol. 2: 327-38.

J.T. Lexicon Knockout Mouse NIH-0750, Mouse Genome Database (MGD), Mouse Genome Informatics Web Site, informatics.jax.org/external/ko/lexicon/1223.html (Jul. 18, 2006).

Kaido et al. (1995), "IFN-alpha 1 gene transfection completely abolishes the tumorigenicity of murine B16 melanoma cells in allogeneic DBA/2 mice and decreases their tumorigenicity in syngeneic C57BL/6 mice." Int. J. Cancer 60: 221-229.

Kamimura et al. (2004), "The IHPK1 gene is disrupted at the 3p21.31 breakpoint of t(3;9) in a family with type 2 diabetes mellitus." J. Hum. Genet. 49: 360-5.

Larsson et al. (1997), "Inhibition of phosphatases and increased Ca2+ channel activity by inositol hexakisphosphate." Science 278: 471-4.

Lee et al. (2007), "Regulation of a cyclin-CDK-CDK inhibitor complex by inositol pyrophosphates." Science 316: 109-12.

(Continued)

*Primary Examiner*—Valarie Bertoglio

(74) *Attorney, Agent, or Firm*—McDonnell Boehnen Hulbert & Berghoff LLP

(57) ABSTRACT

The invention provides reagents and methods for treating type II diabetes, as well as methods for identifying compounds for treating type II diabetes.

13 Claims, 8 Drawing Sheets

OTHER PUBLICATIONS

Leibiger et al. (1998), "Exocytosis of insulin promotes insulin gene transcription via the insulin receptor/PI-3 kinase/p70 s6 kinase and CaM kinase pathways." Mol. Cell. 1(6): 933-938.

Lilja et al. (2004), "Cyclin-dependent kinase 5 associated with p39 promotes Munc18-1 phosphorylation and Ca(2+)-dependent exocytosis." J. Biol. Chem. 279: 29534-41.

Luo et al. (2001), "GRAB: a physiologic guanine nucleotide exchange factor for Rab3A, which interacts with inositol hexakisphosphate kinase." Neuron 31: 439-51.

Marchetti et al. (2006), "The pancreatic beta-cell in human Type 2 diabetes." Nutr. Metab. Cardiovasc. Dis. 16 Suppl 1: S3-6.

Merglen et al. (2004), "Glucose sensitivity and metabolism-secretion coupling studied during two-year continuous culture in INS-1E insulinoma cells." Endocrinology 145: 667-78.

Nagamatsu et al. (2007), "IP7 debut in insulin release." Science 318(5854): 1249-50.

Nagata et al. (2005), "Inositol hexakisphosphate kinase-2, a physiologic mediator of cell death." J. Biol. Chem. 280: 1634-40.

Ogura et al. (1990), "Implantation of genetically manipulated fibroblasts into mice as antitumor alpha-interferon therapy." Cancer Research 50: 5102-5106.

Olofsson et al. (2002), "Fast insulin secretion reflects exocytosis of docked granules in mouse pancreatic B-cells." Pflugers Archiv. 444: 43-51.

Pesesse et al. (2004), "Signaling by higher inositol polyphosphates. Synthesis of bisdiphosphoinositol tetrakisphosphate ("InsP8") is selectively activated by hyperosmotic stress." J. Biol. Chem. 279: 43378-81.

Ray (2007), "InsP7 and insulin release." Sci. STKE 2007(414): tw435.

Reddy et al. (1997), "Synthesis of 2- and 5-diphospho-myo-inositol pentakisphosphate (2- and 5-PP-InsP5), intracellular mediators" Tetrahedron Letters 38: 4951-2.

Rorsman et al. (2003), "Insulin granule dynamics in pancreatic beta cells." Diabetologia 46: 1029-45.

Saiardi et al. (1999), "Synthesis of diphosphoinositol pentakisphosphate by a newly identified family of higher inositol polyphosphate kinases." Curr. Biol. 9: 1323-6.

Saiardi et al. (2001), "Identification and characterization of a novel inositol hexakisphosphate kinase." J. Biol. Chem. 276(42): 39179-85.

Saiardi et al. (2004), "Phosphorylation of proteins by inositol pyrophosphates." Science 306: 2101-5.

Santodonato et al. (1996), "Cure of mice with established metastatic friend leukemia cell tumors by a combined therapy with tumor cells expressing both interferon-alpha 1 and herpes simplex thymidine kinase followed by ganciclovir." Human Gene Therapy 7: 1-10.

Santodonato et al. (1997), "Local and systemic antitumor response after combined therapy of mouse metastatic tumors with tumor cells expressing IFN-alpha and HSVtk: perspectives for the generation of cancer vaccines." Gene Therapy 4: 1246-1255.

Schwarze et al. (1999), "In vivo protein transduction: delivery of a biologically active protein into the mouse." Science 285(5433): 1569-72.

Shears (2004), "How versatile are inositol phosphate kinases?" Biochem. J. 377: 265-80.

Takenawa et al. (2001), "Phosphoinositides, key molecules for regulation of actin cytoskeletal organization and membrane traffic from the plasma membrane." Biochim. Biophys. Acta 1533: 190-206.

Togashi et al. (1997), "Structural identification of the myo-inositol 1,4,5-trisphosphate-binding domain in rat brain inositol 1,4,5-trisphosphate 3-kinase." Biochem. J. 326: 221-5.

Tyagi et al. (2001), "Internalization of HIV-1 tat requires cell surface heparan sulfate proteoglycans." J. Biol. Chem. 276(5): 3254-61.

Vanhaesebroeck et al. (2001), "Synthesis and function of 3-phosphorylated inositol lipids." Ann. Rev. Biochem. 70: 535-602.

Yu et al. (2003), "Cytosolic multiple inositol polyphosphate phosphatase in the regulation of cytoplasmic free Ca2+ concentration." J. Biol. Chem. 278: 46210-8.

SEQUENCE LISTING

```
<160> NUMBER OF SEQ ID NOS: 6

<210> SEQ ID NO 1
<211> LENGTH: 441
<212> TYPE: PRT
<213> ORGANISM: Homo sapiens

<400> SEQUENCE: 1

Met Cys Val Cys Gln Thr Met Glu Val Gly Gln Tyr Gly Lys Asn Ala
1               5                   10                  15

Ser Arg Ala Gly Asp Arg Gly Val Leu Leu Glu Pro Phe Ile His Gln
            20                  25                  30

Val Gly Gly His Ser Ser Met Met Arg Tyr Asp Asp His Thr Val Cys
        35                  40                  45

Lys Pro Leu Ile Ser Arg Glu Gln Arg Phe Tyr Glu Ser Leu Pro Pro
    50                  55                  60

Glu Met Lys Glu Phe Thr Pro Glu Tyr Lys Gly Val Val Ser Val Cys
65                  70                  75                  80
```

-continued

```
Phe Glu Gly Asp Ser Asp Gly Tyr Ile Asn Leu Val Ala Tyr Pro Tyr
                85                  90                  95

Val Glu Ser Glu Thr Val Glu Gln Asp Asp Thr Thr Glu Arg Glu Gln
            100                 105                 110

Pro Arg Arg Lys His Ser Arg Arg Ser Leu His Arg Ser Gly Ser Gly
        115                 120                 125

Ser Asp His Lys Glu Glu Lys Ala Ser Leu Ser Leu Glu Thr Ser Glu
    130                 135                 140

Ser Ser Gln Glu Ala Lys Ser Pro Lys Val Glu Leu His Ser His Ser
145                 150                 155                 160

Glu Val Pro Phe Gln Met Leu Asp Gly Asn Ser Gly Leu Ser Ser Glu
                165                 170                 175

Lys Ile Ser His Asn Pro Trp Ser Leu Arg Cys His Lys Gln Gln Leu
            180                 185                 190

Ser Arg Met Arg Ser Glu Ser Lys Asp Arg Lys Leu Tyr Lys Phe Leu
        195                 200                 205

Leu Leu Glu Asn Val Val His His Phe Lys Tyr Pro Cys Val Leu Asp
    210                 215                 220

Leu Lys Met Gly Thr Arg Gln His Gly Asp Asp Ala Ser Ala Glu Lys
225                 230                 235                 240

Ala Ala Arg Gln Met Arg Lys Cys Glu Gln Ser Thr Ser Ala Thr Leu
                245                 250                 255

Gly Val Arg Val Cys Gly Met Gln Val Tyr Gln Leu Asp Thr Gly His
            260                 265                 270

Tyr Leu Cys Arg Asn Lys Tyr Tyr Gly Arg Gly Leu Ser Ile Glu Gly
        275                 280                 285

Phe Arg Asn Ala Leu Tyr Gln Tyr Leu His Asn Gly Leu Asp Leu Arg
    290                 295                 300

Arg Asp Leu Phe Glu Pro Ile Leu Ser Lys Leu Arg Gly Leu Lys Ala
305                 310                 315                 320

Val Leu Glu Arg Gln Ala Ser Tyr Arg Phe Tyr Ser Ser Ser Leu Leu
                325                 330                 335

Val Ile Tyr Asp Gly Lys Glu Cys Arg Ala Glu Ser Cys Leu Asp Arg
            340                 345                 350

Arg Ser Glu Met Arg Leu Lys His Leu Asp Met Val Leu Pro Glu Val
        355                 360                 365

Ala Ser Ser Cys Gly Pro Ser Thr Ser Pro Ser Asn Thr Ser Pro Glu
    370                 375                 380

Ala Gly Pro Ser Ser Gln Pro Lys Val Asp Val Arg Met Ile Asp Phe
385                 390                 395                 400

Ala His Ser Thr Phe Lys Gly Phe Arg Asp Asp Pro Thr Val His Asp
                405                 410                 415

Gly Pro Asp Arg Gly Tyr Val Phe Gly Leu Glu Asn Leu Ile Ser Ile
            420                 425                 430

Met Glu Gln Met Arg Asp Glu Asn Gln
        435                 440
```

```
<210> SEQ ID NO 2
<211> LENGTH: 4117
<212> TYPE: DNA
<213> ORGANISM: Homo sapiens

<400> SEQUENCE: 2

ccgccatctt gttgttgatc cgtacccagt gggcagcgcc gggagctgga ccaagcggcc      60
```

-continued

```
ggtgagaggc cgctgtagcg gtgctcagcc acctgtgctg cctgccaggg ggcgggccga    120
aacctggagg cccggggggc ccagctcccg tagggagccg tgggcgctcg gtgcccgggc    180
cgggcaggcg tggtatctgt ctgttttgag ggggacagtg atggttacat caacttagtg    240
gcctatcctt atgtggaaag tgagactgtg gaacaggatg acacaacaga acgggagcaa    300
cctcggcgca aacactcccg ccggagcctg caccggtcag gcagtggcag tgaccacaag    360
gaggagaaag ccagcctgtc ccttgagacc tctgagagct cacaggaggc aaagagtccg    420
aaggtggagc tgcacagcca ctcagaggtc cctttccaga tgctagatgg caacagtggc    480
ttgagttctg agaagatcag ccacaacccc tggagcctgc gttgtcacaa gcagcagctg    540
agccgcatgc gctccgagtc caaggaccga aagctctaca agttcctcct gcttgagaac    600
gtggtgcacc acttcaagta cccctgcgtg ttggacctga agatgggcac gcggcagcat    660
ggcgatgacg cgtcagctga gaaggcagcc cggcagatgc ggaaatgcga gcagagcaca    720
tcagccacgc tgggcgtcag ggtctgcggc atgcaggtgt accagctgga cacagggcat    780
tacctctgca ggaacaagta ctatggccgt gggctctcca ttgaaggctt ccgcaatgcc    840
ctctatcaat atctgcacaa tggcctggac ctgcgacgtg acctgtttga gcctatcctg    900
agcaaactgc ggggcctgaa agctgtgctg gagcggcagg cctcttaccg cttctactcc    960
agttccctgc ttgtcatcta tgatggcaag gagtgccggg ctgagtcctg cctggaccgc   1020
cggtctgaga tgcgtctcaa gcacctggac atggtgctcc ctgaggtggc gtcatcctgt   1080
ggccccagca ccagccccag caacaccagc cccgaggcgg gtccctcctc tcagcccaag   1140
gtggatgtcc gcatgattga ctttgcacac agcacattca agggcttccg ggatgacccc   1200
accgtgcatg atgggccaga cagaggctac gtgtttggcc tggagaacct catcagcatc   1260
atggaacaga tgcgggacga gaaccagtag gccctgttct gggcccccag aaccccttcc   1320
tctccactgc aggcagggac cattgttctg aacttgccgt gaggacacac agacttgctt   1380
ttaaagggtt atatttctct ttggtgtaaa ctaaaagaaa tgtttttagc tgtagcctgg   1440
aatccatata tataaagtga aggagggcag accacacgcc ctctcagcca ggctcctcag   1500
ctttgtggct ctgactggtg tgtccaggct gccttaggaa ggaagaggtg cccctggtgg   1560
gcttggcagc agggacaggg tgcccttgga cattggtttc tcttgtctag atctttgaga   1620
tctgtggctg cagggccctg ctgattgtaa ggtaaagccc tgggctggtg cagggcccct   1680
ccacgcccac tcttcccttg ttccccagaa gtagagggct ctgggtgccc atttcttggg   1740
ggctttccag tcttatgctg tgggtgtcag ctagctcttt aataggtgcc ctcagggcac   1800
cacagggctg actgcacaaa gctggaccca tccttcggtc tgaccttagc atggggctag   1860
attaatgaag ctgggctgag gccaacttat ggcagagggc ggcgcctggg ttccccaggc   1920
acctgttggc acgtgacagg ttggcacctg tcctattcct gaaacagcct ctctcaccaa   1980
gttcccttgc ctaagaaggc cactccctcc caccccactg aagtggggga tagtcggtgt   2040
cctagcaggc ctcagggcct ctggtggctc tggcccagac agtatttgca gttcttgtgc   2100
tatgggtggg agtcttcttc ctcaagtttc ggcagctgtg ctgctgctgg atgggctgct   2160
cctcccaggg ctcaagggct gtggtccgct cagggtctca tttccccagg ccaagttcaa   2220
ggcagcagcc ctttgtgagg cgctcttggc cctgggcctg gagggagaac tttaagcttt   2280
tttgctcaca gggacgtggt atgggccctg ggtgcaggtg cccacattct gctaatgaga   2340
gctttgtctg atcagtcctg ggtccatcag tttgtccatg tgtccggctg ccagcccgtc   2400
ccttgggatc cttcccctgg ggtgtagcct tgttcattag tatatactca ttccttcatg   2460
```

-continued

```
ctttcctcag cagaacactt ccacttctga ggtgagcttt tgccccatgc ccttcctcca   2520

caggtgttgc ctttttataa agacctgata gcagaataaa ttggtgtttc cctgttgacc   2580

cagcaccatt tctgtgggcc tagaatatgg ccctcaaccc ttagagtggg gcagtgaggg   2640

cttgaggagt gacccttcct ttctcatggt tttagtcatt ttggctgcca gcccttaatg   2700

gcacagatct gctgcttcta acagatggcc aggaggtgac accgatttca gccattgcca   2760

aggttagcac cctctccttt gagcctaggg ccacactgtt cattgtcact ttaggcaagt   2820

gcctgtttgg ctttaaaggt aagcctgcca gctgtgagaa gccttggtaa ctgatggact   2880

catttcctgg tccttaaaga tgcagcctct taagggctcc ttgatggatg ccatctctcc   2940

tagcccccag ccctggtgcc actggtgggc aggttcccat tctttggggc tgggagggac   3000

agcttgcctg tttctggtca caaattacag tcttctctcc tgtaccattc tgtggcttca   3060

gccatggggg cagtagccct tcattagtgt agatagtcat tccctggtag ggtggagggt   3120

aagacatagg gtctggaact gtttgggacc ttttggggat gtcctgtgcc tcccagattc   3180

ctcgattctg ggaggagagg ctgccgcatt ctgctgctcc tcacagcgag caaagctgca   3240

cccacttaca ttcagtattt tcctggcact acaaagagtg ggaaggcctg ggatttgctg   3300

ctgctccctt agagcagggc ccctcttttc agcactttgg acacctggag acccagccct   3360

gttatttaat ggtagtgggc aagtgtgtgt gcatactgtc tgccactgct ttctccctgc   3420

cccatgccag agagccctgt ccctgccagg cccagccttc ttagccccaa cttgggaaca   3480

aagtgcaaca tgggatcatg ggttggggtg ctcaggtgag ccctctctat agtgcttccc   3540

tgggccaagc tgacaccagc ccctgagggt ggggtgggac gggtggtgct taaaagagga   3600

aggggaccag tgtagcaact tgccagggac cccacccctc cctctctggg cctgtgcagt   3660

gagcatgggg attcccatca aggggcctgg cacctgtgct agttacgtag ccgctgctca   3720

cgcgctcact cctgaccaca tgcacgttcc ctagatgcag actgctttga actttaaagc   3780

tgtacaattt ggttatgttt gtgctgactt aaaatatatt ttaatgagga aaaaataatg   3840

gagaaccctg ggaaggacct ggttcttttg cttctcgggg aactgtaagc cctcgcgttc   3900

tgggaatcgc tctctgctgc tctttcctgg aagctaagcc tgtctccacc gcccgaggcc   3960

tgcgccggtg gctcccgccg cagttgcgtt tgctttggac cttgcgtgcg ggggaggggg   4020

tgctcggtcc gagcccgctc ctttctgtac acctagcgct gcccgccccg cttgtgtctg   4080

aggtcgtgta tgtcaaaaat aaagccgcta gaaacgg                             4117
```

```
<210> SEQ ID NO 3
<211> LENGTH: 4468
<212> TYPE: DNA
<213> ORGANISM: Homo sapiens

<400> SEQUENCE: 3

ccgccatctt gttgttgatc cgtacccagt gggcagcgcc gggagctgga ccaagcggcc     60

ggtgagaggc cgctgtagcg gtgctcagcc acctgtgctg cctgccaggg ggcgggccga    120

aacctggagg cccgggggc ccagctcccg tagggagccg tgggcgctcg gtgcccgggc    180

cgggcaggac agaataataa gctgaataga atctgaccat tggctttcac ctggccagga    240

ccttctatgt agctctcctt ttgtggccca tgtgctgcat cctctgccct cagtgtgcaa    300

ctggccccca acgcaatgtg tgtttgtcaa accatggaag tggggcagta tggcaagaat    360

gcaagtcggg ctggagaccg gggagtcctc ctggagccct tcatccacca agtaggcgga    420
```

-continued

```
cacagcagca tgatgcgtta cgacgatcac actgtgtgca agcccctcat ctcccgggaa    480
cagcgctttt acgagtccct ccctcccgaa atgaaggagt tcacccctga atacaaaggc    540
gtggtatctg tctgttttga gggggacagt gatggttaca tcaacttagt ggcctatcct    600
tatgtggaaa gtgagactgt ggaacaggat gacacaacag aacgggagca acctcggcgc    660
aaacactccc gccggagcct gcaccggtca ggcagtggca gtgaccacaa ggaggagaaa    720
gccagcctgt cccttgagac ctctgagagc tcacaggagg caaagagtcc gaaggtggag    780
ctgcacagcc actcagaggt ccctttccag atgctagatg gcaacagtgg cttgagttct    840
gagaagatca gccacaaccc ctggagcctg cgttgtcaca agcagcagct gagccgcatg    900
cgctccgagt ccaaggaccg aaagctctac aagttcctcc tgcttgagaa cgtggtgcac    960
cacttcaagt accccctgcgt gttggacctg aagatgggca cgcggcagca tggcgatgac   1020
gcgtcagctg agaaggcagc ccggcagatg cggaaatgcg agcagagcac atcagccacg   1080
ctgggcgtca gggtctgcgg catgcaggtg taccagctgg acacagggca ttacctctgc   1140
aggaacaagt actatggccg tgggctctcc attgaaggct tccgcaatgc cctctatcaa   1200
tatctgcaca atggcctgga cctgcgacgt gacctgtttg agcctatcct gagcaaactg   1260
cggggcctga aagctgtgct ggagcggcag gcctcttacc gcttctactc cagttccctg   1320
cttgtcatct atgatggcaa ggagtgccgg gctgagtcct gcctggaccg ccggtctgag   1380
atgcgtctca agcacctgga catggtgctc cctgaggtgg cgtcatcctg tggccccagc   1440
accagcccca gcaacaccag ccccgaggcg ggtccctcct ctcagcccaa ggtggatgtc   1500
cgcatgattg actttgcaca cagcacattc aagggcttcc gggatgaccc caccgtgcat   1560
gatgggccag acagaggcta cgtgtttggc ctggagaacc tcatcagcat catggaacag   1620
atgcgggacg agaaccagta ggccctgttc tgggccccca gaacccctc ctctccactg   1680
caggcaggga ccattgttct gaacttgccg tgaggacaca cagacttgct tttaaagggt   1740
tatatttctc tttggtgtaa actaaaagaa atgtttttag ctgtagcctg gaatccatat   1800
atataaagtg aaggagggca gaccacacgc cctctcagcc aggctcctca gctttgtggc   1860
tctgactggt gtgtccaggc tgccttagga aggaagaggt gcccctggtg ggcttggcag   1920
cagggacagg gtgcccttgg acattggttt ctcttgtcta gatctttgag atctgtggct   1980
gcagggccct gctgattgta aggtaaagcc ctgggctggt gcagggcccc tccacgccca   2040
ctcttccctt gttccccaga agtagagggc tctgggtgcc catttcttgg gggctttcca   2100
gtcttatgct gtgggtgtca gctagctctt taataggtgc cctcagggca ccacagggct   2160
gactgcacaa agctggaccc atccttcggt ctgaccttag catggggcta gattaatgaa   2220
gctgggctga ggccaactta tggcagaggg cggcgcctgg gttccccagg cacctgttgg   2280
cacgtgacag gttggcacct gtcctattcc tgaaacagcc tctctcacca agttcccttg   2340
cctaagaagg ccactccctc ccaccccact gaagtggggg atagtcggtg tcctagcagg   2400
cctcagggcc tctggtggct ctggcccaga cagtatttgc agttcttgtg ctatgggtgg   2460
gagtcttctt cctcaagttt cggcagctgt gctgctgctg gatgggctgc tcctcccagg   2520
gctcaagggc tgtggtccgc tcagggtctc atttccccag gccaagttca aggcagcagc   2580
cctttgtgag gcgctcttgg ccctgggcct ggagggagaa ctttaagctt ttttgctcac   2640
agggacgtgg tatgggccct gggtgcaggt gcccacattc tgctaatgag agctttgtct   2700
gatcagtcct gggtccatca gtttgtccat gtgtccggct gccagcccgt cccttgggat   2760
ccttcccctg gggtgtagcc ttgttcatta gtatatactc attccttcat gctttcctca   2820
```

-continued

```
gcagaacact tccacttctg aggtgagctt ttgccccatg cccttcctcc acaggtgttg   2880

ccttttata aagacctgat agcagaataa attggtgttt ccctgttgac ccagcaccat   2940

ttctgtgggc ctagaatatg gccctcaacc cttagagtgg ggcagtgagg gcttgaggag   3000

tgacccttcc tttctcatgg ttttagtcat tttggctgcc agcccttaat ggcacagatc   3060

tgctgcttct aacagatggc caggaggtga caccgatttc agccattgcc aaggttagca   3120

ccctctcctt tgagcctagg gccacactgt tcattgtcac tttaggcaag tgcctgtttg   3180

gctttaaagg taagcctgcc agctgtgaga agccttggta actgatggac tcatttcctg   3240

gtccttaaag atgcagcctc ttaagggctc cttgatggat gccatctctc ctagccccca   3300

gccctggtgc cactggtggg caggttccca ttctttgggg ctgggaggga cagcttgcct   3360

gtttctggtc acaaattaca gtcttctctc ctgtaccatt ctgtggcttc agccatgggg   3420

gcagtagccc ttcattagtg tagatagtca ttccctggta gggtggaggg taagacatag   3480

ggtctggaac tgtttgggac cttttgggga tgtcctgtgc ctcccagatt cctcgattct   3540

gggaggagag gctgccgcat tctgctgctc ctcacagcga gcaaagctgc acccacttac   3600

attcagtatt ttcctggcac tacaaagagt gggaaggcct gggatttgct gctgctccct   3660

tagagcaggg cccctctttt cagcactttg gacacctgga gacccagccc tgttatttaa   3720

tggtagtggg caagtgtgtg tgcatactgt ctgccactgc tttctccctg ccccatgcca   3780

gagagccctg tccctgccag gcccagcctt cttagcccca acttgggaac aaagtgcaac   3840

atgggatcat gggttggggt gctcaggtga gccctctcta tagtgcttcc ctgggccaag   3900

ctgacaccag cccctgaggg tggggtggga cgggtggtgc ttaaaagagg aaggggacca   3960

gtgtagcaac ttgccaggga ccccacccct ccctctctgg gcctgtgcag tgagcatggg   4020

gattcccatc aaggggcctg gcacctgtgc tagttacgta gccgctgctc acgcgctcac   4080

tcctgaccac atgcacgttc cctagatgca gactgctttg aactttaaag ctgtacaatt   4140

tggttatgtt tgtgctgact taaaatatat tttaatgagg aaaaaataat ggagaaccct   4200

gggaaggacc tggttctttt gcttctcggg gaactgtaag ccctcgcgtt ctgggaatcg   4260

ctctctgctg ctctttcctg gaagctaagc ctgtctccac cgcccgaggc ctgcgccggt   4320

ggctcccgcc gcagttgcgt ttgctttgga ccttgcgtgc gggggagggg gtgctcggtc   4380

cgagcccgct cctttctgta cacctagcgc tgcccgcccc gcttgtgtct gaggtcgtgt   4440

atgtcaaaaa taaagccgct agaaacgg                                       4468
```

<210> SEQ ID NO 4
<211> LENGTH: 28
<212> TYPE: DNA
<213> ORGANISM: Artificial
<220> FEATURE:
<223> OTHER INFORMATION: Synthetic

<400> SEQUENCE: 4

```
gtgtgctgga cttggccatg ggtacccg                                         28
```

<210> SEQ ID NO 5
<211> LENGTH: 27
<212> TYPE: DNA
<213> ORGANISM: Artificial
<220> FEATURE:
<223> OTHER INFORMATION: Synthetic

<400> SEQUENCE: 5

-continued

```
gtccttgacc tcgcgatggg cacacga                                         27


<210> SEQ ID NO 6
<211> LENGTH: 39
<212> TYPE: DNA
<213> ORGANISM: Artificial
<220> FEATURE:
<223> OTHER INFORMATION: Synthetic

<400> SEQUENCE: 6

ccctgtgtcc tggatctggc catggggacc cggcagcac                            39
```

INOSITOL PYROPHOSPHATES DETERMINE EXOCYTOTIC CAPACITY

CROSS REFERENCE

This application claims priority to U.S. Provisional Patent Application Ser. No. 60/969,443 filed Aug. 31, 2007, incorporated by reference herein in its entirety.

BACKGROUND OF THE INVENTION

Phosphoinositides, in both their water-soluble and lipid forms, have a prominent role in cellular signal-transduction events. Important events are the generation of inositol 1,4,5-trisphosphate (Ins(1,4,5)P3) and its regulation of intracellular Ca2+ homeostasis (1) and the 3-phosphorylated inositol lipid products of phosphatidylinositol (PI3 kinase) (2), with diverse roles in mitogenesis, apoptosis and vesicle trafficking. Phosphatidylinositol 4,5-bisphosphate (PtdIns (4,5)P2), the major source of these two signalling systems, is not merely a precursor for the above signal transduction pathways but plays in itself significant roles in vesicle trafficking, exocytosis, cytoskeletal rearrangements and regulation of ion channels (3). In the last decade there has also been a growing appreciation that highly phosphorylated inositol polyphosphates, distant derivatives of the Ins(1,4,5)P3 second messenger, play a role in signal-transduction and cellular regulation (4-6). Perhaps the most exciting new vista that has opened concerns the role of diester derivatives of both inositol pentakis- and hexakisphosphates (InsP5 and InsP6). The pyrophosphate derivatives of InsP6 diphosphoinositol pentakisphosphate, and bis-(diphospho)inositol tetrakisphosphate are commonly referred to as 'InsP7' and 'InsP8'. These inositol pyrophosphate derivatives rapidly turnover and are estimated to have similar free energy of hydrolysis as ATP (4). A striking consequence of this high-energy phosphate group is the ability of InsP7 to directly phosphorylate a subset of proteins in an ATP- and enzyme-independent manner (7). The variety of cellular responses, apparently controlled by these molecules (4,8) may be facilitated by the differential intracellular distribution of the kinases that make them (9). The concentrations of inositol pyrophosphates can be dynamically regulated during key cellular events, underscoring their importance for cell function. For example, InsP7 levels change during cell cycle progression (10) and InsP7 regulates cyclin/CDK complexes (11) whereas InsP8 increases acutely in response to cellular stress (8). However, recent work has also demonstrated a role for InsP6 as an enzymatic co-factor and so by analogy, it is possible that even under non-stimulatory conditions, InsP7 could be an important regulatory molecule.

Phosphoinositides are also key regulators of the insulin secreting pancreatic β-cell (12). These cells are critical players in blood glucose homeostasis and act by coupling increases in the concentration of glucose and other circulatory or neuronal-derived regulators, to the exocytosis of insulin. The highly phosphorylated InsP6 is particularly interesting as it has been shown to activate voltage-dependent L-type Ca2+ channels (13), exocytosis (14,15) and dynamin-mediated endocytosis (16), all key processes in insulin secretion. A role for InsP7 in the β-cell has not yet been determined. However, given the suggested involvement of inositol pyrophosphates in vesicle trafficking (4), the critical nature of such trafficking events for the process of insulin exocytosis and the high β-cell concentration of InsP6 (13), the immediate precursor of InsP7, we postulated that inositol pyrophosphates may play a significant role in the β-cell. We now demonstrate a novel role for InsP7 in the regulation of insulin exocytosis.

SUMMARY OF THE INVENTION

In one aspect, the present invention provides methods for treating type II diabetes comprising administering to a patient with type II diabetes an effective amount of a therapeutic capable of increasing expression of IP6K1 kinase.

In another aspect, the present invention provides methods for stimulating insulin exocytosis from pancreatic beta cells comprising administering to a patient in need thereof an effective amount of a therapeutic capable of increasing expression IP6KI kinase.

In another aspect, the present invention provides methods for treating type II diabetes comprising administering to a patient with type II diabetes an effective amount of a therapeutic capable of increasing production of $InsP_7$.

In a further aspect, the present invention provides methods for identifying a compound for treating type II diabetes comprising:

(a) contacting pancreatic beta cells with one or more test compounds; and (b) determining expression level of IP6K1 kinase and/or levels of InsP7;

wherein an increase in the expression of IP6K1 kinase and/or an increase in InsP7 indicates that the compound is suitable for treating type II diabetes.

DETAILED DESCRIPTION OF THE INVENTION

Figure 1:
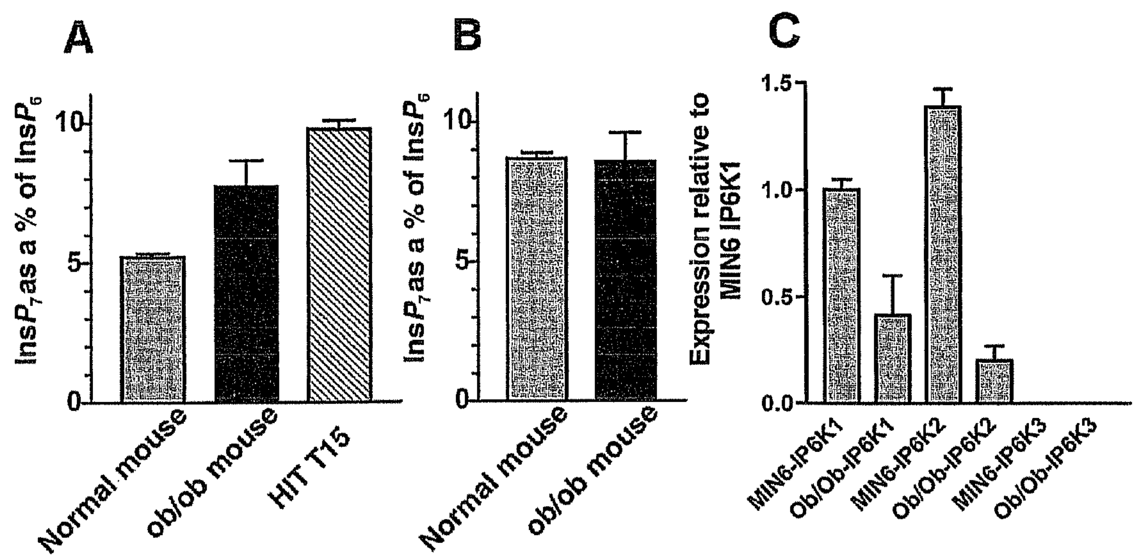
FIG. 1. High basal levels of InsP7 are present in pancreatic β cells and IP6K's are expressed in these cells. (A) Comparison of [3H]-labeled InsP7 as a percentage of [3H]-labeled InsP6 in primary pancreatic islets or insulin secreting MIN6m9 cells. Data are from 3 separate experiments. (B) The islet data from (A) were transformed to take into account the different B-cell composition of normal (60%) vs. ob/ob (90%), islets. (C). Total RNA was extracted from islets and MIN6m9 cells and reverse transcribed. Relative expression of messenger RNA was measured by quantitative Real time PCR using appropriate primers and probes. Primers and probe for 18S rRNA (TaqMan Ribosomal RNA Control Reagents, Applied Biosystems) were used as endogenous control.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2$^{nd}$* Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

In one aspect, the present invention provides methods for treating type II diabetes comprising administering to a subject with type II diabetes an amount effective to treat type II diabetes of a therapeutic capable of increasing InsP7 in pancreatic beta cells of the subject.

In a further aspect, the present invention provides methods for treating type II diabetes comprising administering to a subject with type II diabetes an amount effective to treat type II diabetes of a therapeutic capable of increasing expression of IP6K1 kinase in pancreatic beta cells of the subject.

As the inventors have demonstrated in the attached, the pancreatic β-cell maintains high levels of InsP7. This pyrophosphate then serves as an essential player in the insulin secretory process by regulating the readily releasable pool of insulin-containing granules and thereby maintaining the immediate exocytotic capacity of the β-cell. The inventors further showed that endogenous InsP7 generated by IP6K1 is responsible for the enhanced exocytotic capacity in pancreatic beta-cells. Thus, therapeutics capable of increasing expression of IP6K1 kinase can be used to treat type II diabetes by generating InsP7, resulting in increased exocytotic capacity in pancreatic beta cells.

In one embodiment, the therapeutic comprises a gene therapy vector directing expression of IP6K1 or active fragments thereof. (Protein accession information: Q 92551

(SEQ ID NO: 1); cDNA accession information (Alternative splice variants) 1. NM_153273.3 (SEQ ID NO: 3), 2. NM_001006115 (SEQ ID NO: 2)) comprises a gene therapy vector directing expression of IP6K1 or active fragments thereof. The gene therapy method comprises administration of a nucleic acid construct capable of expressing IP6K1 or active fragments thereof in the subject, and preferably in pancreatic beta cells of the subject. In one example, the cDNA sequences may be operably linked with an insulin promoter (Leibiger, Mol. Cell. 1: 933-938 (1998)). Such gene therapy and delivery techniques are known in the art; see, for example, WO90/11092, which is herein incorporated by reference, or: M. I. Phillips (Ed.): Gene Therapy Methods. Methods in Enzymology, Vol. 346, Academic Press, San Diego 2002. Thus, for example, cells from the subject may be engineered ex vivo with a nucleic acid construct comprising a promoter operably linked to the nucleic acid molecule corresponding to the molecule to be introduced, with the engineered cells then being provided to the subject to be treated. Such methods are well-known in the art. For example, see Belidegrun, A., et al., J. Natl. Cancer Inst. 85: 207-216 (1993); Ferrantini, M. et al., Cancer Research 53: 1107-1112 (1993); Ferrantini, M. et al., J. Immunology 153: 4604-4615 (1994); Kaido, T., et al., Int. J. Cancer 60: 221-229 (1995); Ogura, H., et al., Cancer Research 50: 5102-5106 (1990); Santodonato, L., et al., Human Gene Therapy 7: 1-10 (1996); Santodonato, L., et al., Gene Therapy 4: 1246-1255 (1997); and Zhang, J.-F. et al., Cancer Gene Therapy 3: 31-38 (1996)), which are herein incorporated by reference. The cells which are engineered may be, for example, pancreatic beta cells.

The nucleic acid molecules may also be delivered as a naked nucleic acid molecule. The term "naked" nucleic acid molecule refers to sequences that are free from any delivery vehicle that acts to assist, promote or facilitate entry into the cell, including viral sequences, viral particles, liposome formulations, lipofectin or precipitating agents and the like. However, the nucleic acid molecules used in gene therapy can also be delivered in liposome formulations and lipofectin formulations and the like that can be prepared by methods well known to those skilled in the art. Such methods are described, for example, in U.S. Pat. Nos. 5,593,972, 5,589,466, and 5,580,859, which are herein incorporated by reference.

The naked nucleic acid molecules are delivered by any method known in the art, including, but not limited to, direct needle injection at the delivery site, intravenous injection, topical administration, catheter infusion, and so-called "gene guns". These delivery methods are known in the art. The constructs may also be delivered with delivery vehicles such as viral sequences, viral particles, liposome formulations, lipofectin, precipitating agents, etc.

In another embodiment, the therapeutic comprises IP6K1 or active fragments thereof. The polypeptides can be administered via any suitable technique, including but not limited to delivery as a conjugate with a transduction domain, which are one or more amino acid sequence or any other molecule that can carry an active domain across cell membranes. These domains can be linked to other polypeptides to direct movement of the linked polypeptide across cell membranes. (See, for example, *Cell* 55: 1179-1188, 1988; *Cell* 55: 1189-1193, 1988; *Proc Natl Acad Sci U S A* 91: 664-668, 1994; *Science* 285: 1569-1572, 1999; *J Biol Chem* 276: 3254-3261, 2001; and *Cancer Res* 61: 474-477, 2001)

In a further aspect, the present invention provides methods for identifying a compound for treating type II diabetes comprising:

(a) contacting pancreatic beta cells with one or more test compounds; and (b) determining expression level of IP6K1 kinase and/or levels of InsP7;

wherein an increase in the expression of IP6K1 kinase and/or an increase in InsP7 indicates that the compound is suitable for treating type II diabetes.

As noted above, therapeutics capable of increasing expression of IP6K1 kinase can be used to treat type II diabetes by generating InsP7, resulting in increased exocytotic capacity in pancreatic beta cells. Thus, compounds that can be used to increase expression of IP6K1 kinase and/or InsP7 in pancreatic beta cells can be used to treat type II diabetes.

Determining expression levels of IP6K1 kinase and/or an increase in InsP7 in the pancreatic beta cells can be performed using any technique in the art, including but not limited to those disclosed in the examples that follow.

As used herein, "basal glucose conditions" mean a glucose concentration of between 1 and 6 mM glucose; in one embodiment, 3 mM glucose is used. As is understood by those of skill in the art, basal glucose concentration may vary between species. Basal glucose concentration can be determined for any particular cell or tissue type by those conditions that do not induce changes in, for example, cytoplasmic free $Ca^{2+}$ concentration or insulin release.

As used herein, "pancreatic β cells" are any population of cells that contains pancreatic β islet cells. The cells can be obtained from any mammalian species, or may be present within the mammalian species when the assays are conducted in vivo. Such pancreatic β islet cell populations include the pancreas, isolated pancreatic islets of Langerhans ("pancreatic islets"), isolated pancreatic β islet cells, and insulin secreting cell lines. Methods for pancreatic isolation are well known in the art, and methods for isolating pancreatic islets, can be found, for example, in Cejvan et al., Diabetes 52: 1176-1181 (2003); Zambre et al., Biochem. Pharmacol. 57: 1159-1164 (1999), and Fagan et al., Surgery 124: 254-259 (1998), and references cited therein. Insulin secreting cell lines are available from the American Tissue Culture Collection ("ATCC") (Rockville, Md.). In a further embodiment where pancreatic β cells are used, they are obtained from ob/ob mice, which contain more than 95% β cells in their islets.

In order to derive optimal information on the ability of the one or more test compounds to increase in the expression of IP6K1 kinase and/or an increase in InsP7 in pancreatic beta cells, it is preferred to compare IP6K1 kinase and/or InsP7 levels ion experimental cells with levels from control cells. Such control cells can include one or more of the following:

1. The same host cells, treated in the same way except not contacted with the one or more test compounds;

2. The same host cells, treated in the same way except contacted with the one or more test compounds at different time points (for analyzing time-dependent effects); and 3. The same host cells, treated in the same way except contacted with different concentrations of the one or more test compounds (for analyzing concentration-dependent effects);

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other then polypeptides, antibodies, or nucleic acids, such compounds can be made by any of the variety of methods in the art for conducting organic chemical synthesis.

Test compounds identified as increasing the expression of IP6K1 kinase and/or an increase in InsP7 in the pancreatic beta cells can be further assessed for use as a candidate compound for treating type II diabetes using any further technique, including but not limited to contacting pancreatic beta cells with the test compounds and measuring insulin release induced by the test compounds, and/or by measuring resulting pancreatic beta cell capacitance induced by the test compounds; those compounds that increase insulin release and/or capacitance (which is a measure of insulin exocytosis as described below) compared to control may be of particular value as candidate compounds for treating type II diabetes. In a further embodiment, measuring capacitance is performed as described below, and those test compounds that elicit an exocytotic response at the first depolarization are considered good candidate compounds for treating type II diabetes.

EXAMPLES

Materials and Methods

Reagents and constructs. 5-Diphosphoinositol pentakisphosphate (InsP7) was synthesized as described previously (25). The ORF for IP6K1, IP6K2 and IP6K3, were obtained by digestion using SalI-NotI pCMV-IP6K1, pCMV-IP6K2 (26) and by digestion using SalI pGST-IP6K3 (27. The purified ORF were subcloned in the eukaryotic expression vector pCMV-Myc (Clontech). Kinase-dead versions were prepared as follows. Previous studies have identified a lysine in InsP3KA that is critical for catalytic activity (28). In mouse IP6K1, human IP6K2 and human IP6K3 this lysine occurs at position 226, 222 and 217, respectively. For IP6K1 we mutated lysine 226 to alanine using the following oligo: K26A, 5'-GTGTGCTGGACTTGGCCATGGGTACCCG-3' (SEQ ID NO: 4) and complement. For IP6K2 we mutated lysine 222 to alanine using the following oligo: K222A, 5'-GTCCTTGACCTCGCGATGGGCACACGA-3' (SEQ ID NO: 5) and complement. For IP6K3 we mutated lysine 217 to alanine using the following oligo: K217A, 5'-CCCTGTGTCCTGGATCTGGCCATGGGGACCCGGCAGCAC-3' (SEQ ID NO: 6) and complement.

Constructs were tested in INS-1E cells to establish their efficacy. IP6K1-3 and their respective catalytically inactive forms were transfected into INS-1E cells (protocols below). All constructs were expressed at similar level, as judged by western blotting. Moreover, IP6K1-3 wt, but not their catalytically inactive forms (K/A) increased cellular InsP7 up to 6-fold.

RNAi's were obtained from Ambion Inc (Austin, Tex.) and the following RNAi ID's were used to silence IP6K's. RNAi's to IP6K1 (1, siRNAi ID=188560) and (4, siRNAi ID=71758). RNAi's for IP6K2 (3, siRNA ID=287702) and (5, siRNA ID=292211). Non-targeting controls (1, siRNA ID 4611) and (2, siRNA ID=4613) were used as negative controls. These siRNA's were also supplied by Ambion with Cy3 fluorescent tags and used in the primary mouse beta cell experiments.

RNA Extraction and Real Time-PCR

Total RNAs were extracted from cells using the RNeasy™ Micro Kit (Qiagen Inc, Valencia, Calif.). The RNAs were digested with DNase I for 1 hour at 37° C. (Fermentas, St. Leon Rot, Germany) and then re-purified with RNeasy™ Micro Kit (Qiagen Inc). The Applied Biosystem MultiScribe™ Reverse Transcriptase kit was used to reverse transcribe 1 μg of purified RNA according to manufacture's instructions. 3.94 μl of the resulting cDNAs from the reverse transcriptase reaction were diluted in 10.06 μl sterile water and 1.25 μl aliquots of each sample were tested in triplicate for each different quantitative PCR reaction. Relative expression of messenger RNA was measured by quantitative RT-PCR (with TaqMan Gene Expression Assays products on an ABI PRISM™ 7700 Sequence Detection System, Applied Biosystems, Foster City, Calif.). For the analysis, the following TaqMan™ assays (Applied Biosystems) were used: for IP6K1: inositol hexaphosphate kinase 1, for IP6K2: inositol hexaphosphate kinase 2 and for IP6K3: inositol hexaphosphate kinase 3. Primers and probe for 18S rRNA (TaqMan™ Ribosomal RNA Control Reagents, Applied Biosystems) were used as endogenous control.

Cell Culture and Transfection

HIT T15 cells and mouse islets were maintained in RPMI-1640 medium as described previously (29). Labeling was undertaken with [3H] myo-inositol (GE Healthcare, Amersham Biosciences, Uppsala, Sweden) 10 or 50 μCi/ml for insulin-secreting HIT T15 cells and islets respectively in a special RPMI-1640 medium, described previously (29). Cells were labeled for 72 h and labeling from 48-168 h did not change the InsP6 to InsP7 ratio. For experiments, islets or cells were transferred with washing into a Krebs buffer and incubated for 30 min under basal glucose conditions (0.1 mM for cell lines and 3 mM for islets). Inositol polyphosphates were extracted and separated on HPLC as described previously (29). INS-1E cells were cultured as described elsewhere (30). Mouse pancreatic islets were isolated from female NMRI mice (Bomholtgaard, Ry, Denmark) or normoglycemic ob/ob mice as previously described (31,32). Cells were incubated in RPMI 1640 medium (Invitrogen Corporation, Carlsbad, Calif.) supplemented with 10% (v/v) heat-inactivated fetal calf serum, 100 IU/ml penicillin and 100 μg/ml streptomycin. Single mouse islet cells were transfected adherently the day after plating with pIRES2-EGFP (mock) or a combination of pIRES2-EGFP and construct of interest at 2 μg/ml in the above RPMI 1640 cell culture medium using Lipofectamine™ 2000 (Invitrogen Corporation, Carlsbad, Calif.) according to manufacture's instructions. Lipofectamine™ was used in a ratio of 4:1 to DNA. Cells were used 48 h after transfection. Based on GFP fluorescence, the transfection efficiency in mouse islet cells amounted to 8+/−1% (n=124 cells; 4 different cell preparations and transfections). SiRNA's were transfected into MIN6m9 cells and primary islet cells using Lipofectamine™ 2000 and Opti-.MEM™ media. The medium was changed the following day into normal culture media for either MIN6m9 cells or primary islet cells and the cells cultured for a further 4 days.

Capacitance Measurements

Cells expressing EGFP were selected for capacitance measurements. Exocytosis was monitored as changes in cell capacitance using either the perforated patch or standard whole-cell configuration of the patch-clamp technique and an EPC9 patch-clamp amplifier (Heka Elektronik, Lambrecht/Pfalz, Germany). The pipette solution for the perforated patch configuration consisted of (in mM) 76 Cs2SO4, 10 NaCl, 10 KCl, 1 MgCl2, 5 HEPES (pH 7.35 with CsOH) and 0.24 mg/ml amphotericin B. Perforation required a few minutes, and the voltage clamp was considered satisfactory when the Gseries (series conductance) was stable and >35 nS. The pipette solution used for standard whole-cell recordings contained (in mM) 125 Cs-glutamate, 10 CsCl, 10 NaCl, 1 MgCl2, 5 HEPES, 0.05 EGTA, 0.01 GTP and 3 MgATP (pH 7.15 using CsOH). InsP7 isomers were dissolved in the pipette-filling solution to the final concentrations indicated in the text and kept on ice until use. The extracellular medium was composed of (in mM) 118 NaCl, 20 tetraethylammonium-Cl, 5.6 KCl, 1.2 MgCl2, 2.6 CaCl2, 5 HEPES (pH 7.40 using NaOH) and 3 glucose. The stimulation protocol consisted of trains of four 500-ms depolarizations applied at 1 Hz and went from −70 mV to zero mV. The capacitance measurements were performed at 33° C. and the recording chamber was perfused at a rate of 1.5 ml/min.

Measurement of Single L-Type Ca2+ Channel Activity

Cell-attached patch recordings were performed in control MIN6m9 cells and those subjected to IP6K1-siRNA as described previously (32). Briefly, typical electrode resistance was 2-4 MΩ. Cell-attached single-channel recordings were made with Ba2+ as the charge carrier (in mM): 110 BaCl2, 10 TEA-Cl, 5 HEPES-Ba(OH)2 and pH 7.4 and a depolarizing external recording solution, containing (in mM) 125 KCl, 30 KOH, 10 EGTA, 2 CaCl2, 1 MgCl2, 5 HEPES-KOH and pH 7.15, is used to bring the intracellular potential to ~0 mV. Recordings are made with an Axopatch™ 200 amplifier (Axon Instruments, Foster City, Calif.). Voltage pulses (200 ms) are applied at a frequency of 0.5 Hz to depolarize cells from a holding potential of −70 mV to a membrane potential of 0 mV. Resulting currents are filtered at 1 kHz, digitized at 5 kHz and analyzed with the software program pCLAMP™ 6 (Axon Instruments, Foster City, Calif., U.S.A.).

Human Growth Hormone (hGH) Release Assay.

After transfection with pCMV5-hGH and either empty vector pcDNA3 or plasmid of interest, INS-1E cells were seeded into 48-multiwell plates ($2\times10^5$ cells per well) and cultured for 48 h. Incubation and secretion experiments were performed as described (33) using the same extracellular medium as described above and supplemented with 3 mM glucose. hGH levels in the various samples were measured using ELISA (Roche, Mannheim, Germany).

Statistical analysis. Results are presented as mean values±S.E.M. for indicated number of experiments. Statistical significances were evaluated using Dunnett's test for multiple comparisons to a control and Tukey's test when multiple comparisons between groups were required.

Results

Using [3H] myo-inositol labelling protocols we examined insulin-secreting cells and pancreatic islets for the presence of inositol pyrophosphate species. InsP7 was identified by its co-elution with a bone fide InsP7 standard generated using InsP6 kinase (data not shown). Very little InsP8 was detectable. FIG. 1A shows InsP7 levels expressed as a percentage of cellular InsP6 levels for an insulin-secreting cell line or primary β-cells. In normal mouse pancreatic islets (60% β-cells), the relative level of InsP7 is about 5% of the InsP6 level. In contrast, the percentage of InsP7 in islets from ob/ob mice, which have more than about 90% β-cells, is about 8%. This suggests that the elevated InsP7 levels are restricted to the -cells. Normalizing the primary mouse data to 100% β-cells (FIG. 1B) suggests that they maintain InsP7 levels at about 9% of the InsP6 concentration. Of the insulin secreting cell lines, only HIT-T15 cells have a similar level of InsP7 (10% of InsP6). Using the equilibrium labelling techniques (13) which can only be reliably applied to growing, cultured cells, we were able to estimate the basal concentration of InsP7 in HIT-T15 cells to be 5.8+/−0.14 μM, (±SEM, n=3), reflecting a concentration at the top end of the range that has been estimated in other mammalian cells or yeast (1-5 μM) (4). Since InsP7 is in a state of rapid exchange with the cellular InsP6 pool in β-cells (data not shown) in common with other mammalian cells (4) and the cellular concentration of InsP6 in β-cells is also high (13), it is perhaps not surprising that high levels of InsP7 exist in these cells.

An important caveat is that the high InsP7 is a cell-wide average which doesn't take into account separate cellular compartments. This is particularly important as one of the main isoforms of InsP6 kinase, IP6K2, can be nuclear (9) and thus the InsP7 it produces may not influence events in the cytosol or plasma membrane, for example vesicle trafficking or exocytosis, respectively. Therefore, using Taqman™-based quantitative Real time PCR we examined islet and β-cell lysates for the presence of IP6K isoforms. FIG. 1C demonstrates the expression of IP6K1 and IP6K2, but not IP6K3. Expression levels for the two kinases were similar in a given cell type, however, the expression of IP6K1 and 2 was lower in the primary cells compared to the cell line MIN6, perhaps reflecting the fact that InsP7 metabolism is up-regulated during the cell cycle (10,11). Thus the high InsP7 levels are not likely to reflect an exclusive nuclear pool but are likely to be consistently high throughout the cell and thus could influence insulin secretion.

Figure 2:
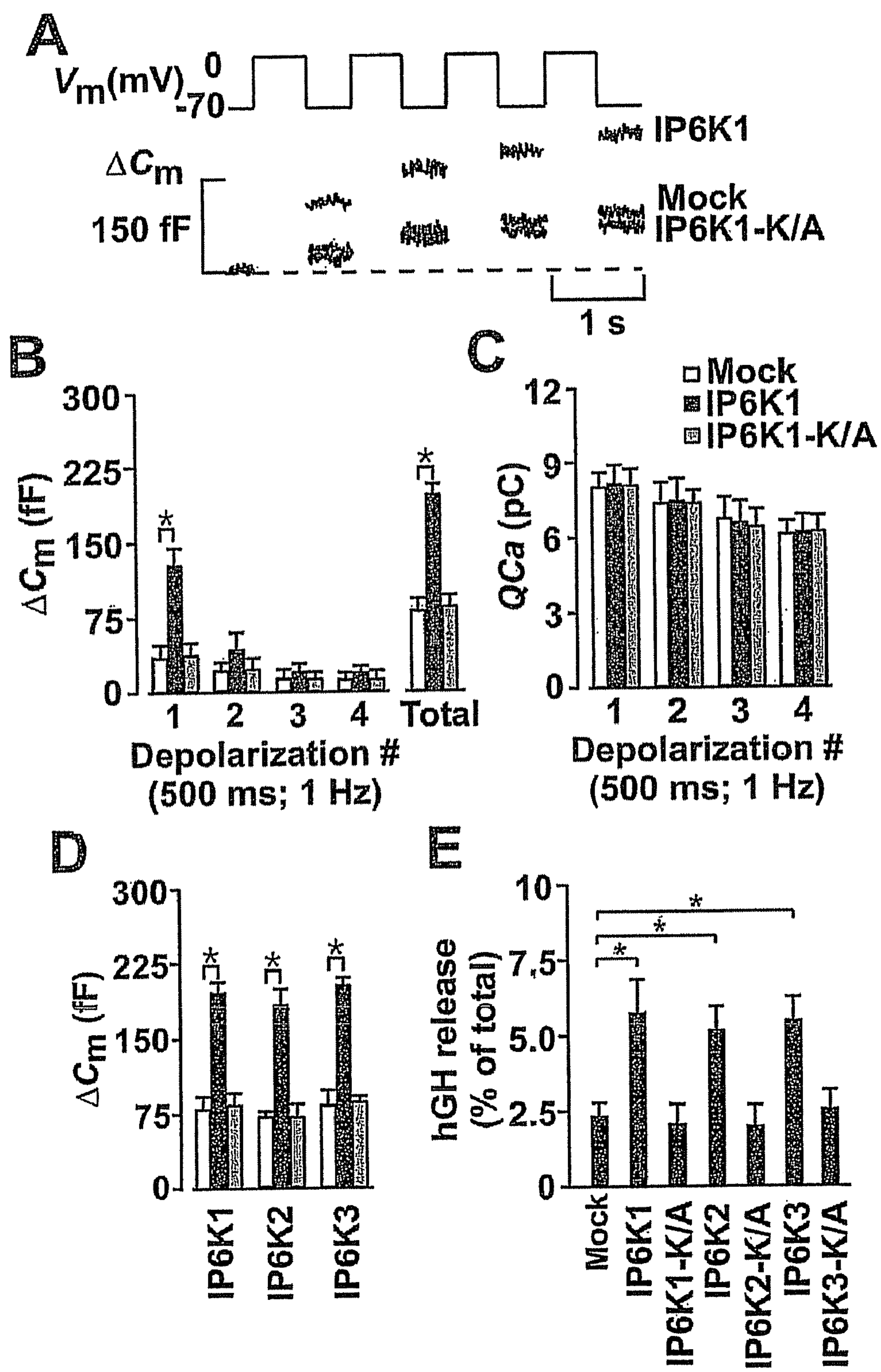
FIG. 2. Expression of IP6K's promote exocytosis in pancreatic β-cells. IP6K1 stimulates Ca2+-dependent exocytosis. (A) Individual mouse β-cells were transfected with EGFP (mock) or a combination of EGFP and either a wild-type (IP6K1) or a kinase-dead (IP6K1-K/A) variant of IP6K and subjected to a train of four 500-ms depolarizations using the perforated patch configuration. Increases in cell capacitance (ΔCm) were measured at 3 mM glucose in the extracellular medium. (B) Histogram summarizing the average increase in cell capacitance plotted against the individual depolarizations as well as the total increase in cell capacitance at the end of the train in cells mock transfected or overexpressing either wild-type (IP6K1) or kinase-dead (IP6K1-K/A) IP6K. (C) Histogram showing integrated Ca2+ current (QCa) plotted against the individual depolarizations in cells mock transfected or overexpressing either wild-type or IP6K1-K/A. Values are from 8-12 experiments. *$P<0.05$. (D) Histogram summarizing the average total increase in cell capacitance at the end of the train in mock transfected cells or cells overexpressing either wild-type (IP6Kn) or kinase-dead (IP6Kn-K/A) type 1, 2 and 3 kinases, respectively. Values are from 7-12 experiments. *P<0.05. (E) INS-1E cells were co-transfected in parallel with pCMV5-hGH and empty vector (pcDNA3) (mock) or with pCMV5-hGH and either wild-type (IP6Kn) or, kinase-dead (IP6Kn-K/A), types 1, 2 and 3 kinases, respectively. hGH secretion was measured in Krebs-Ringer bicarbonate HEPES buffer with 3 mM glucose. hGH release is depicted as secreted hGH in percentage of total hGH. Values from 3 experiments (each in triplicate). *P<0.05.

To investigate whether high InsP7 concentrations are responsible for keeping β-cells in a responsive state, we over-expressed all 3 reported mammalian IP6K's in primary β-cells under basal conditions and examined whether stimulated exocytosis was subsequently enhanced. We used increases in cell capacitance as a measure of exocytosis. This technique detects the increase in β-cell surface area that occurs when the insulin-containing granules fuse with the plasma membrane (17). The perforated patch whole-cell technique was used to allow measurements in metabolically intact cells and exocytosis was elicited by trains consistent of four 500-ms depolarizing pulses from −70 mV to 0 mV. In mock transfected cells, the capacitance increase elicited by the train amounted to 79+/−11 fF (n=8; FIGS. 2A, B). In cells overexpressing IP6K1 the amplitude of the capacitance increase was stimulated by 153% and averaged 198+/−12 fF (P<0.05; n=10), whereas no effect on exocytosis was observed in cells overexpressing a kinase-dead version of IP6K1 (FIGS. 2A, B). Interestingly, the capacitance increase evoked by the first depolarization was augmented by 293% in cells overexpressing wild-type IP6K1. Exocytosis during the first depolarization is believed to largely represent the content of the readily releasable pool (RRP)(18). The size of the RRP (in fF) can be estimated using the equation: RRP=S/(1-R2), where S is the sum of the response to the first (ΔC1) and the second (ΔC2) pulse and R is the ratio ΔC2/ΔC1 (18). We estimate that the RRP averaged 96+/−9 fF (n=8) and 225+/−21 fF (n=10) in mock and wildtype IP6K1 transfected cells, respectively. Thus, IP6K1 increased the size of the RRP by 134%. Using a conversion factor of 3 fF per granule (19), it can be estimated that the RRP contains 30 and 75 granules in mock and wildtype IP6K1 transfected cells, respectively. The stimulatory action of IP6K1 is restricted to the first depolarization and little enhancement is seen during the final three pulses (FIG. 2B). The exhaustion of the exocytotic response during the train is unlikely to reflect inactivation of the Ca2+ current with resulting suppression of Ca2+-induced exocytosis (FIG. 2C).

FIG. 2D shows that the ability of wild-type IP6K1 to stimulate exocytosis is shared by IP6K2 and IP6K3. Overexpression of a kinase-dead version of IP6K 2 and IP6K3 did not affect the exocytotic capacity compared to mock transfected cells (FIG. 2D). To confirm a role of IP6K's in the control of exocytosis, we tested the effect of their overexpression in INS-1E cells using the hGH transient co-transfection assay, in which hGH acts as a reporter of exocytosis from transfected cells only. INS-1E cells represent a suitable cell system since total increases in cell capacitance in cells overexpressing IP6K1 were comparable to those observed in primary mouse β cells (data not shown). Overexpression of IP6K1-3 stimulated hGH secretion 150% above basal (P<0.05; n=9-12), an effect that was not shared by their kinase-dead mutants. (FIG. 2E). Based on the fact that only IP6K1 and 2 are present in β-cells, these and not IP6K3 are likely modulators of exocytosis.

Figure 3:
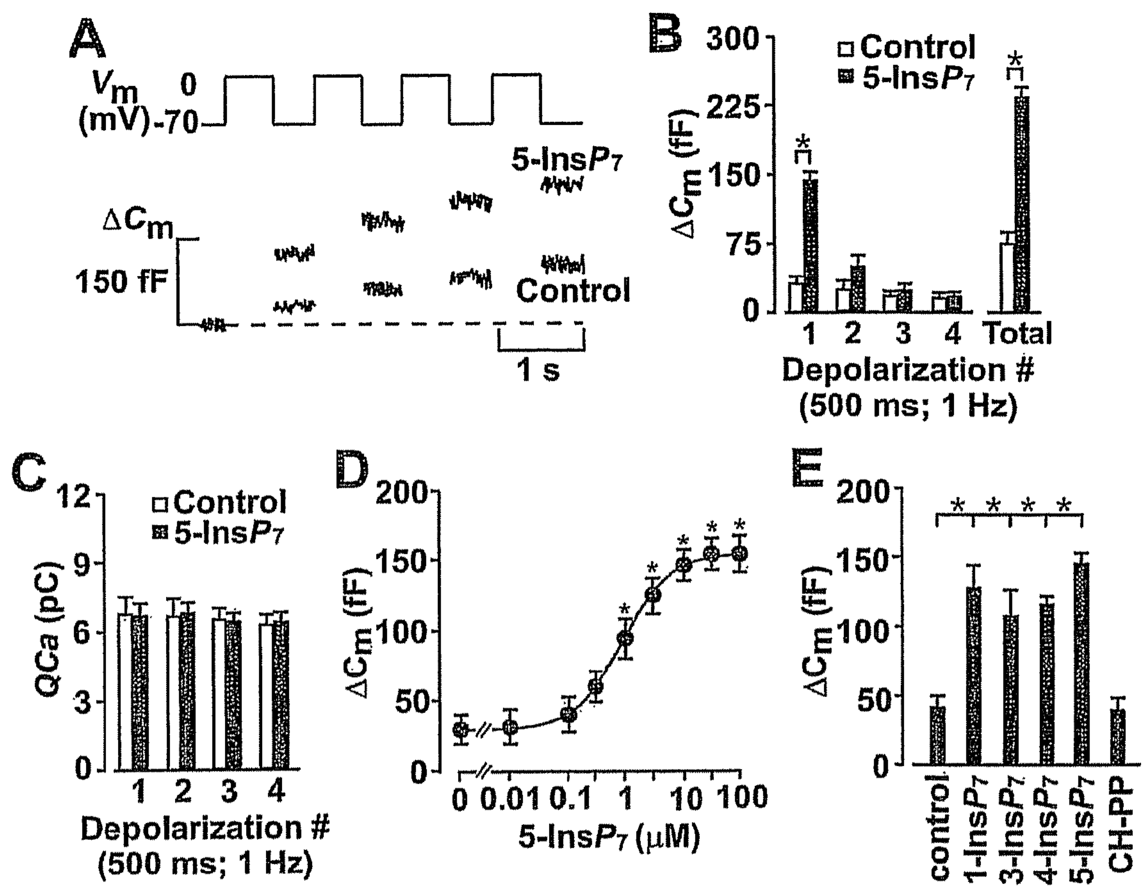
FIG. 3. InsP7 dose-dependently promotes Ca2+-dependent exocytosis. Individual mouse β-cells were subjected to a train of four 500-ms depolarizations using the standard whole-cell patch configuration. (A) Exocytosis was observed under control conditions and in the presence of 3 μM 5-InsP7 in the pipette-filling solution. 5-InsP7 was allowed to diffuse into the cell for 2 min before initiation of the experiment. (B) Histogram summarizing the average increases in cell capacitance plotted against the individual depolarizations as well as the total increases in cell capacitance at the end of the train in the absence or presence of 3 μM 5-InsP7 in the pipette-filling solution. (C) Histogram showing integrated Ca2+ current (QCa) plotted against the individual depolarizations in the absence or presence of 3 μM InsP7 in the pipette-filling solution. (D) Concentration dependence of stimulatory action of 5-InsP7 on exocytosis evoked by a single membrane depolarization from −70 mV to zero. The curve represents a least-squares fit of the mean data points to the Hill equation. Values are from 5-7 experiments. *P<0.05. (E) A comparison of several isomers of InsP7 at a 10 μM concentration on exocytosis using the same protocols as in (A) above.
Figure 4:
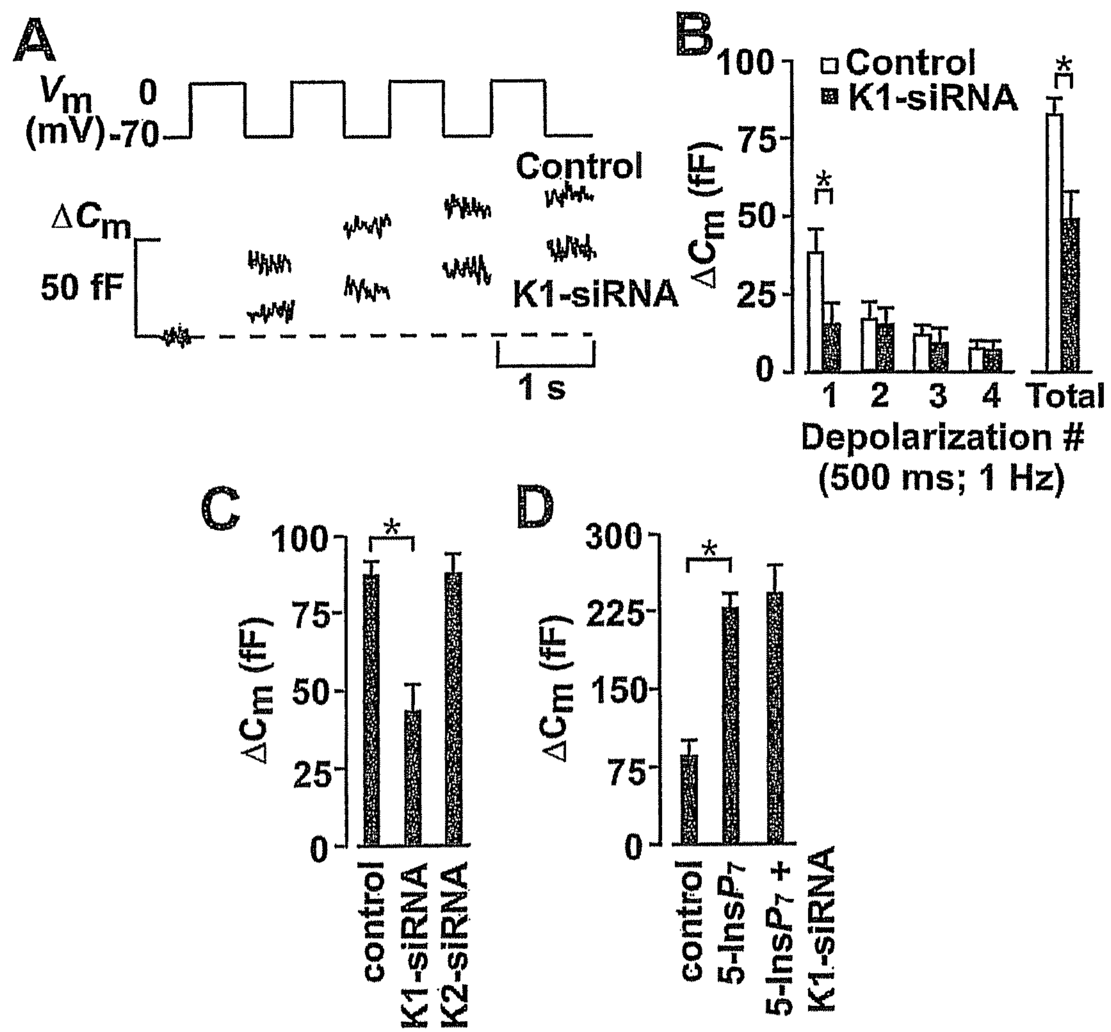
FIG. 4. RNA silencing of IP6K1 but not IP6K2 inhibits release of granules from the RRP. (A) Individual mouse β-cells were transfected with siRNA to IP6K1 (No. 1) at 25 nM or a negative control at the same concentration and subjected to a train of four 500-ms depolarizations using the perforated patch configuration. Increases in cell capacitance (ΔCm) were measured at 3 mM glucose in the extracellular medium. (B) Histogram summarizing the average increases in cell capacitance plotted against the individual depolarizations as well as the total increase in cell capacitance at the end of the train in cells mock transfected or overexpressing either siRNA to IP6K1 or negative control. (C) Effect on total capacitance increase following RNA silencing of IP6K1 and IP6K2. (D) Effect of 5-InsP7 on exocytosis in under control conditions and in cells with reduced expression levels of IP6K1.
Figure 5:
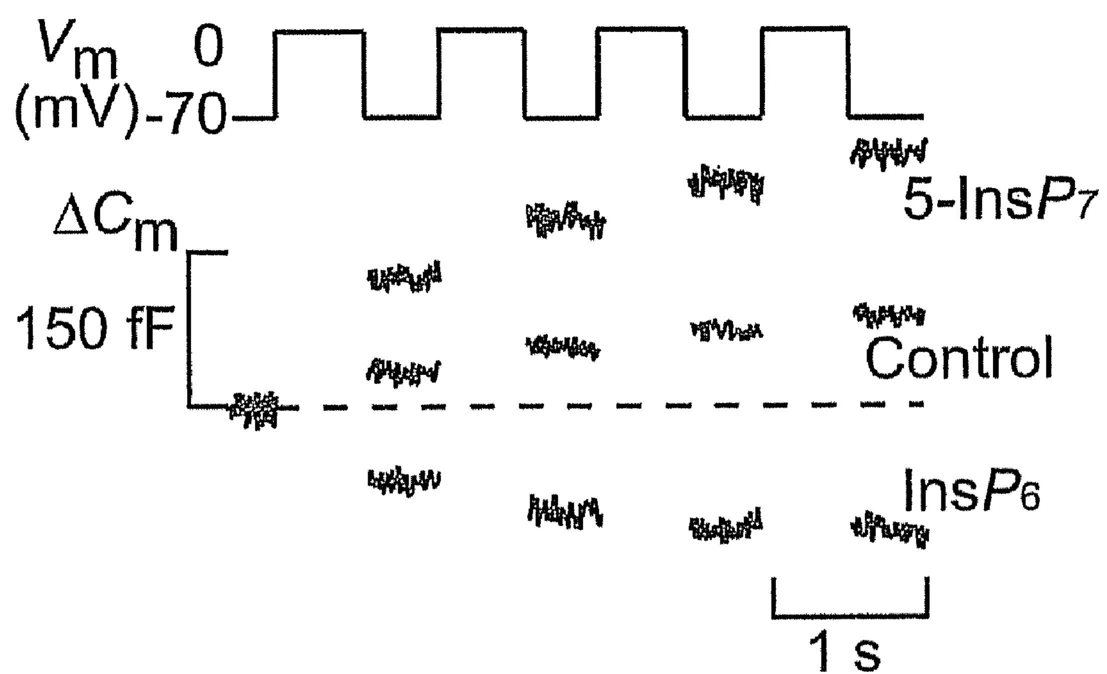
FIG. 5. Effect of 5-InsP7 on exocytosis is distinct from InsP6. Individual mouse cells were subjected to a train of four 500-ms depolarizations using the standard whole-cell patch configuration. Exocytosis was observed under control conditions and in the presence of either 3 μM 5-InsP7 or 10 μM InsP6 in the pipette-filling solution. The inositol phosphates were allowed to diffuse into the cell for 2 min before initiation of the experiment.

An important concern is that IP6K's can also use InsP5 as a substrate, generating a different subset of inositol pyrophosphates (4). Therefore, it was necessary to verify that InsP7 is able to directly promote exocytosis. The mammalian InsP7 is the 5-isomer and this was used in detailed experiments (FIG. 3A-D). We also assessed other theoretical isomers of InsP7 (FIG. 3E). To measure the effects of 5-InsP7 on exocytosis, we applied trains of depolarizations in standard whole-cell experiments where the β-cell was dialyzed with a solution containing 3 μM InsP7. Following establishment of the whole-cell configuration, the cell was allowed two minutes equilibration period. A train consisting of four 500 ms depolarizations from −70 mV to 0 mV was then applied to evoke exocytosis. In a series of six experiments, the total increase in cell capacitance amounted to 231+/−12 fF (P<0.01) in the presence of 3 μM InsP7 in the pipette-filling solution and 77+/−11 fF under control conditions, respectively (FIG. 3A). As was the case for cells overexpressing IP6K1-3 the capacitance increase evoked by the first depolarization in the presence of 5-InsP7 was strongly stimulated with only little effect on exocytosis in response to the subsequent 3 depolarizations (FIG. 3B). The ability of 5-InsP7 to stimulate exocytosis was not associated with a change in the whole-cell Ca2+ current (FIG. 3C). The stimulatory action of 5-InsP7 on exocytosis was concentration dependent (FIG. 3D). No stimulation of exocytosis was observed at ≦0.1 M InsP7. At higher concentrations, 5-InsP7 stimulated exocytosis by 90-410%. Approximating the average data points to the Hill equation yielded a half-maximal stimulatory effect of 1.02 μM and a co-operativity factor of 1.5. Maximal stimulation of exocytosis was observed at concentrations of InsP7≧10 μM, which produced >380% stimulation (FIG. 4D). Thus, 5-InsP7 dose-dependently enhances exocytosis within the physiological range of InsP7 concentrations (1-10 μM). Other isomers of InsP7 were also able to stimulate exocytosis at 10 μM, however CH-PP, a simple pyrophosphate based on cyclohexane, was ineffective (FIG. 4E). Under the conditions used to examine InsP7's effect on exocytosis, the net effect of InsP6 was to promote endocytosis not exocytosis (see FIG. 5). This is because the effect of InsP6 on exocytosis can only be discerned under conditions in which endocytosis is inhibited (15). This is not the case for InsP7. Furthermore, the effect of InsP6 on exocytosis, when endocytosis is inhibited, does not selectively promote secretion from the RRP (data not shown). Our data illustrate that InsP7 and InsP6 have distinct effects on exocytosis. These experiments and those involved in overexpression of kinases do not preclude a role for a more phosphorylated pyrophosphate i.e. InsP8, however since this pyrophosphate is either at a very low concentration or undetectable in β-cells (data not shown), it is unlikely to play a physiological role.

Figure 6:
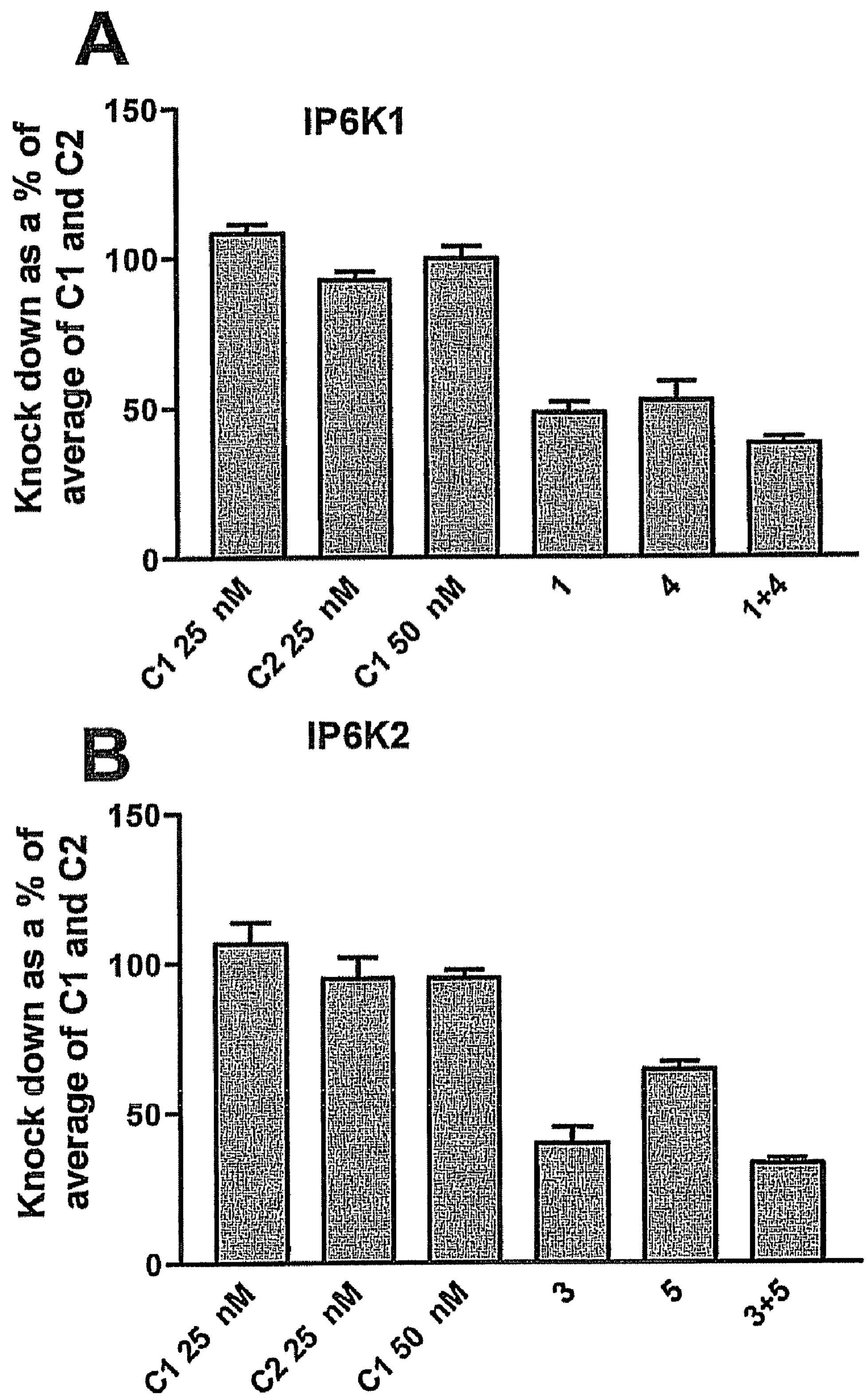
FIG. 6. Screening siRNA's in MIN6 m9 cells. Six siRNA's for each IP6K were screened for their ability to silence at 100 nM in MIN6m) cells. Two in each case IP6K1 (1 and 4) and IP6K2 (3 and 5) were then used in individually or in combination to silence IP6K1 or IP6K2 respectively. This was compared to 2 negative controls. mRNA was extracted and the expression of the genes quantified using Taqman™ RT-PCR. Data are averages±SEM, n=3)

All our data to this point indicate a role for InsP7 in regulated exocytosis, however our results are based on exogenous addition of either enzymes or InsP7. To test whether endogenous InsP7 contributes to the exocytotic capacity in a physiologically relevant manner, we silenced IP6K1 and IP6K2 in -cells using siRNA. Mouse-specific siRNA's were screened using the mouse -cell line, MIN6 and Taqman™ Real time PCR gene expression assays (see FIG. 6). Elimination of either IP6K1 or IP6K2 significantly reduced cellular InsP7 levels (see FIG. 7). Suitable siRNA candidates were fluorescently tagged and transfected into primary β-cells. Cell capacitance measurements on fluorescent cells using the perforated patch technique described above were carried out. Interestingly, only the silencing of IP6K1 but not IP6K2 (FIG. 4C) inhibited the exocytotic capacity, and the effect of silencing was again most pronounced on the first pulse reflecting depletion of the RRP of granules (FIGS. 4A,B). Furthermore, addition of 5-InsP7 in the whole cell mode when the IP6K1 had been silenced was able to restore normal exocytotic response (FIG. 4D). Thus endogenous InsP7 generated by IP6K1 but not IP6K2 is responsible for the enhanced exocytotic capacity in pancreatic -cells. The discrepancy between our exogenous vs. endogenous systems may reflect a differential distribution or cellular associations of the 2 kinases in vivo. Indeed IP6K1 can associate with proteins involved in exocytosis which IP6K2 cannot (20). Interestingly, other studies looking at the role of IP6K2 in apoptosis indicate a similar pattern (21). That is, substantial overexpression of IP6K1-3 leads to an increase in apoptosis, however only the silencing of IP6K2 prevents it. In both cases the supra physiological increase of InsP7 clearly overcomes some compartmentalization exhibited by the different kinases.

Figure 7:
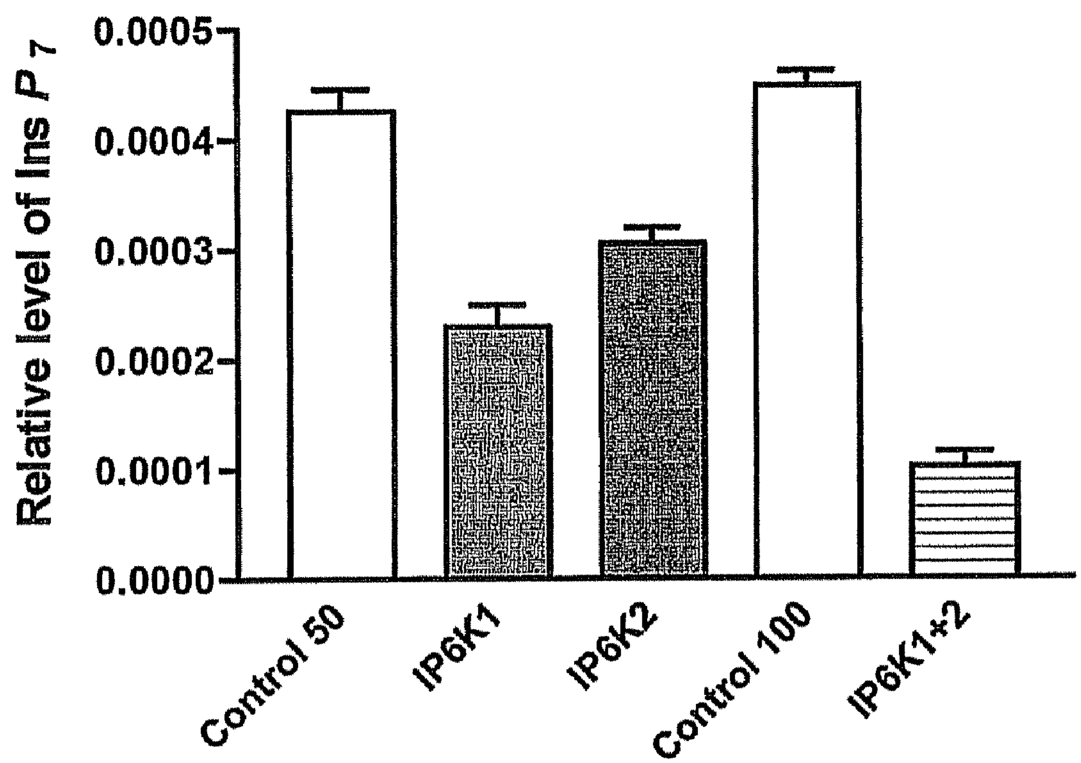
FIG. 7. RNA silencing of IP6K1 or IP6K2 lowers cellular InsP7 levels. MIN6 m9 cells were transfected with selected siRNA for either negative control or IP6K1 and 2. SiRNA's for IP6K1 (1 and 4) were added at 25 nM each. Similar concentrations of the 2 siRNA's for IP6K2 (3 and 5) were added. This was controlled by addition of a 50 nM of a negative control. All 4 siRNA's were also applied simultaneously and controlled with 100 nM negative control siRNA. Two hours after transfection with siRNA medium was changed to a 50 μCi/ml [3H]-inositol containing medium and cells were cultured for 48 h to 72 h. Cells were extracted and subjected to HPLC. Data are expressed relative to total inositol lipid and are means from 3 separate experiments SEM, n=3).
Figure 8:
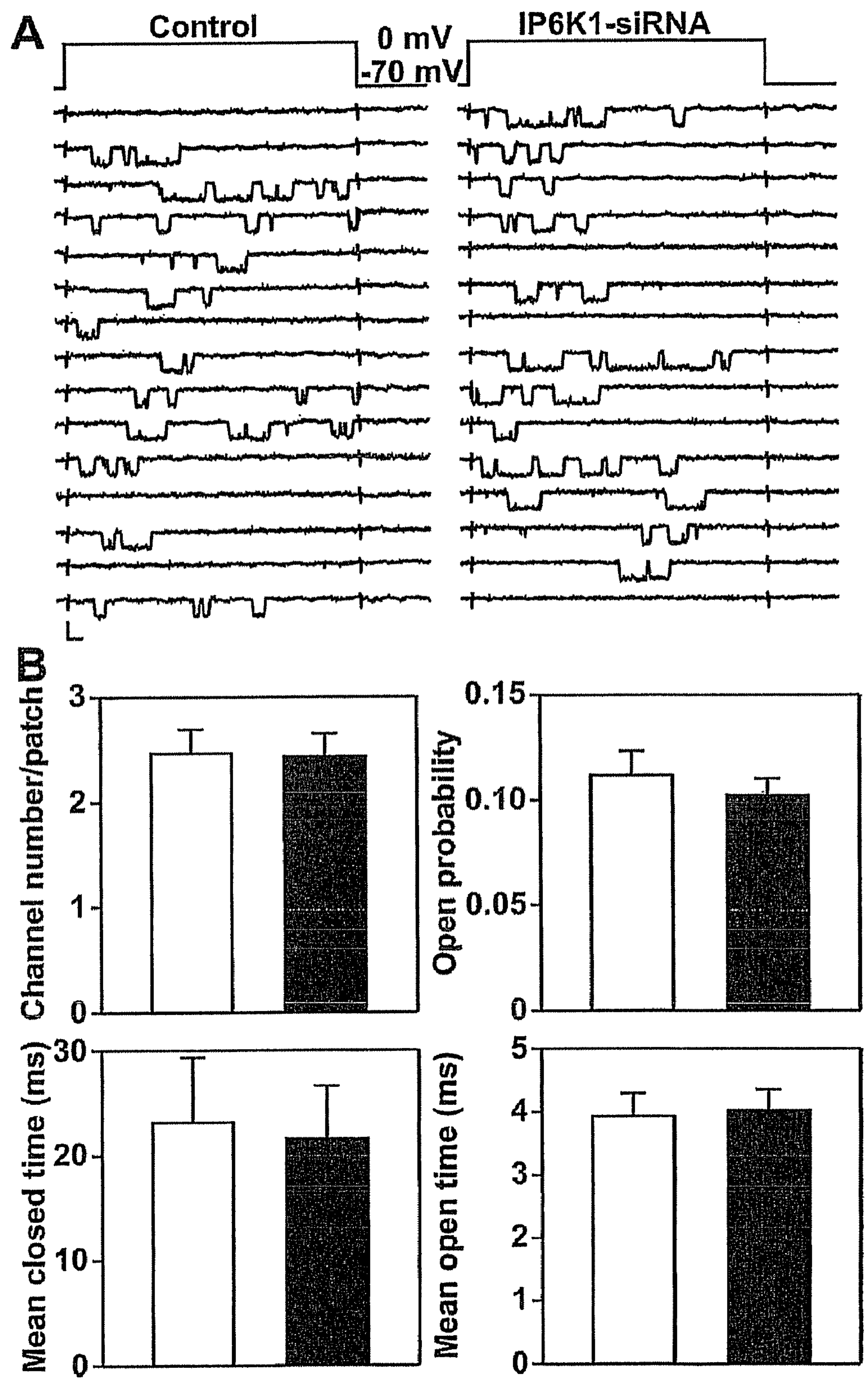
FIG. 8. Effect of IP6K1-siRNA on single L-type Ca2+ channel activity in MIN6 m9 cells. MIN6 m9 cells were transfected with selected siRNA for either negative control 50 nM or siRNA's for IP6K1 (1 and 4) at 25 nM each. (A) Examples of single Ca2+ channel currents recorded from cell-attached patches on a control cell (negative control siRNA transfection, left) and a cell subjected to IP6K1-siRNA (right). Both patches contain one L-type Ca2+ channel. (B) Single L-type Ca2+ channel current parameters in control MIN6 m9 cells (n=30) and those subjected to IP6K1-siRNA (n=30). There is no significant difference in channel number per patch, open probability, mean closed time and mean open time between control MIN6 m9 cells and those subjected to IP6K1-siRNA (P>0.05). Data are presented as means±SEM. Statistical significance was evaluated by either Mann-Whitney U test or unpaired Student's t-test.

One possible mechanistic explanation for the effect of 5-InsP7 on exocytosis may be direct stimulation of voltagegated L-type Ca2+ channel activity, as previously shown for InsP6 (13). Although the whole-cell Ca2+ channel data speak against this (FIGS. 2C and 3C), a detailed analysis was made applying the cell-attached patch configuration, maintaining an intact intracellular milieu, in MIN6m9 cells subjected to IP6K1-siRNA, which significantly decreases intracellular InsP7 (FIG. 7). As shown in FIG. 8, IP6K1 siRNA did not significantly alter channel number per patch, open probability, mean closed time and mean open time (P>0.05). Hence, InsP7 does not affect L-type Ca2+ channel activity, which in striking contrast to InsP6 (13).

In summary, the pancreatic β-cell maintains high levels of InsP7. This pyrophosphate then serves as an essential player in the insulin secretory process by regulating the readily releasable pool of insulin-containing granules and thereby maintaining the immediate exocytotic capacity of the β-cell. An important question for the future is whether disruption of InsP7 metabolism plays any role in the pathogenesis of type 2 diabetes, a disease characterized by a secretory defect in the pancreatic β-cell (22). In this respect, hints are provided by the putative disruption of the IP6K1 gene in a Japanese family with type 2 Diabetes (23) and the reduction of both plasma insulin levels and glucose tolerance in mice in which the IP6K1 gene has been deleted (24).

REFERENCES

1. M. J. Berridge, *Ann N Y Acad Sci.* 766, 31 (1995).
2. B. Vanhaesebroeck et al, *Annu Rev Biochem.* 70, 535 (2001).
3. T. Takenawa, T. Itoh, *Biochim Biophys Acta.* 1533, 190 (2001).
4. M. Bennett, S. M. Onnebo, C. Azevedo, A. Saiardi, *Cell Mol Life Sci.* 63, 552 (2006).
5. R. F. Irvine, M. J. Schell, *Nat Rev Mol Cell Biol.* 2, 327 (2001).
6. S. B. Shears, *Biochem J.* 377, 265 (2004).
7. A. Saiardi, R. Bhandari, A. C. Resnick, A. M. Snowman, S. H. Snyder, *Science.* 306, 2101 (2004).
8. X. Pesesse, K. Choi, T. Zhang, S. B. Shears, *J Biol Chem.* 279, 43378 (2004).
9. A. Saiardi, E. Nagata, H. R. Luo, A. M. Snowman, S. H. Snyder, *J Biol Chem.* 276, 39179 (2001).
10. C. J. Barker, J. Wright, P. J. Hughes, C. J. Kirk, R. H. Michell, *Biochem J.* 380, 465 (2004).
11. Y. S. Lee, S. Mulugu, J. D. York, E. K. O'Shea, *Science* 316 109 (2007).
12. C. J. Barker, I. B. Leibiger, B. Leibiger, P.-O. Berggren, *Am J Physiol Endocrinol Metab.* 283, E1113 (2002).
13. O. Larsson et al., *Science.* 278, 471 (1997).
14. A. M. Efanov, S. V. Zaitsev, P.-O. Berggren, *Proc Natl Acad Sci USA.* 94, 4435 (1997).
15. M. Hoy, P.-O. Berggren, J. Gromada, *J Biol Chem.* 278, 35168 (2003).
16. M. Hoy. et al., *Proc Natl Acad Sci USA.* 99, 6773 (2002).
17. P. Rorsman P, E. Renstrom *Diabetologia.* 46, 1029 (2003).
18. K. D. Gillis, R. Mossner, E. Neher, *Neuron* 16, 1209 (1996).
19. C. S. Olofsson. et al., *Pflügers Archiv* 444, 43 (2002).
20. H. R. Luo et al., *Neuron.* 31, 439 (2001).
21. E. Nagata et al. *J Biol Chem.* 280, 1634-40 (2005)
22. P. Marchetti, S. Del Prato, R. Lupi, S. Del Guerra, Nutr *Metab Cardiovasc Dis.* 16 Suppl 1: S3 (2006).
23. J. Kamimura et al., *J Hum Genet.* 49, 360 (2004).
24. J. T. Lexicon Knockout Mouse NIH-0750, Mouse Genome Database (MGD), Mouse Genome Informatics Web Site, informatics.jax.org/external/ko/lexicon/1223.html (18 Jul. 2006).
25. K. M. Reddy, K. K. Reddy, J. R. Falck, *Tetrahedron Letters* 38, 4951 (1997)
26. A. Saiardi, H. Erdjument-Bromage, A. M. Snowman, P. Tempst, S. H. Snyder, *Curr. Biol* 9, 1323 (1999).
27. A. Saiardi, E. Nagata, H. R. Luo, A. M. Snowman, S. H. Snyder, *J Biol Chem.* 276, 39179 (2001).
28. S. Togashi, K. Takazawa, T. Endo, C. Erneux, T. Onaya, *Biochem. J.* 326, 221 (1997).
29. O. Larsson et al., *Science.* 278, 471 (1997).
30. A. Merglen et al., *Endocrinology* 145, 667 (2004).
31. M. Hoy et al., *Proc Natl Acad Sci USA.* 99, 6773 (2002).
32. J. Yu et al., *J. Biol. Chem.* 278, 46210 (2003).
33. L. Lilja et al., *J. Biol. Chem.* 279, 29534 (2004).

We claim:

1. A method of screening for compounds that increase exocytosis in pancreatic beta cells comprising:

(a) contacting pancreatic beta cells in vitro with one or more test compounds; and (b) determining an expression level of IP6K1 kinase and/or a level of InsP7 in the pancreatic beta cells;

wherein a test compound-induced increase in the expression level of IP6K1 kinase and/or a test compound-induced increase in InsP7 levels relative to control indicates that the test compound is suitable for increasing exocytosis in pancreatic beta cells.

2. The method of claim 1, wherein the contacting occurs under basal glucose conditions.

3. The method of claim 1, wherein the pancreatic beta cells are selected from the group consisting of pancreatic tissue, isolated pancreatic islets of Langerhans, isolated pancreatic β islet cells, and insulin secreting cell lines.

4. The method of claim 1, wherein the pancreatic beta cells comprise isolated pancreatic islets of Langerhans.

5. The method of claim 1, further comprising measuring pancreatic beta cell capacitance induced by the one or more test compounds and comparing to control.

6. The method of claim 1, wherein the method comprises determining the expression level of IP6K1 kinase in the pancreatic beta cells.

7. The method of claim 1, wherein the method comprises determining the level of InsP7 in the pancreatic beta cells.

8. The method of claim 2, wherein the method comprises determining the expression level of IP6K1 kinase in the pancreatic beta cells.

9. The method of claim 3, wherein the method comprises determining the expression level of IP6K1 kinase in the pancreatic beta cells.

10. The method of claim 4, wherein the method comprises determining the expression level of IP6K1 kinase in the pancreatic beta cells.

11. The method of claim 2, wherein the method comprises determining the level of InsP7 in the pancreatic beta cells.

12. The method of claim 3, wherein the method comprises determining the level of InsP7 in the pancreatic beta cells.

13. The method of claim 4, wherein the method comprises determining the level of InsP7 in the pancreatic beta cells.

* * * * *